United States Patent
Feng

(10) Patent No.: US 9,421,155 B2
(45) Date of Patent: Aug. 23, 2016

(54) TWO-PART TOOTH WHITENING COMPOSITION AND SYSTEM, AND METHODS OF USING THE SAME

(71) Applicant: GOSMILE, INC., Berkeley, CA (US)

(72) Inventor: Jianxun Feng, Santa Maria, CA (US)

(73) Assignee: GOSMILE, INC., Berkeley, CA (US)

( * ) Notice: Subject to any disclaimer, the term of this patent is extended or adjusted under 35 U.S.C. 154(b) by 0 days.

(21) Appl. No.: 13/804,866

(22) Filed: Mar. 14, 2013

(65) Prior Publication Data

US 2013/0251646 A1 Sep. 26, 2013

Related U.S. Application Data

(60) Provisional application No. 61/613,955, filed on Mar. 21, 2012.

(51) Int. Cl.
*A61K 8/24* (2006.01)
*A61K 8/22* (2006.01)
*A61Q 11/00* (2006.01)

(52) U.S. Cl.
CPC ... *A61K 8/24* (2013.01); *A61K 8/22* (2013.01); *A61Q 11/00* (2013.01); *A61K 2800/882* (2013.01)

(58) Field of Classification Search
CPC .......... A61K 8/046; A61K 8/22; A61Q 11/00
USPC ...................................... 424/44, 53
See application file for complete search history.

(56) References Cited

U.S. PATENT DOCUMENTS

| | | | |
|---|---|---|---|
| 3,216,463 A * | 11/1965 | Kibbel, Jr. et al. | 141/3 |
| 4,592,489 A | 6/1986 | Simon et al. | |
| 4,849,213 A | 7/1989 | Schaeffer | |
| 5,038,963 A | 8/1991 | Pettengill et al. | |
| 5,252,312 A * | 10/1993 | Gentile et al. | 424/49 |
| 5,928,628 A | 7/1999 | Pellico | |
| 6,312,670 B1 | 11/2001 | Montgomery | |
| 6,322,773 B1 | 11/2001 | Montgomery | |
| 6,488,913 B2 | 12/2002 | Orlowski et al. | |
| 6,514,543 B2 | 2/2003 | Montgomery | |
| 6,536,628 B2 | 3/2003 | Montgomery | |
| 6,746,664 B2 | 6/2004 | Allred | |
| 6,986,883 B2 * | 1/2006 | Pellico | 424/53 |
| 7,201,577 B2 | 4/2007 | Levine | |
| 7,802,988 B2 | 9/2010 | Yarborough | |
| 2006/0198803 A1 * | 9/2006 | Giniger | 424/70.4 |

OTHER PUBLICATIONS

Go Smile Double Action 3 to 12 Day Teeth Whitening System, downloaded from the Internet at <http://www.qvc.com/Go-Smile-Double-Action-Teeth-Whitening-System-w24-Ampoules.product.A218279.html> (Oct. 2011 product first aired on QVC).

* cited by examiner

*Primary Examiner* — Walter Webb
(74) *Attorney, Agent, or Firm* — Marshall, Gerstein & Borun LLP

(57) ABSTRACT

A tooth whitening composition includes an aqueous activation part comprising a peroxide activating component, and a peroxide part comprising a peroxide component that does not contain a peroxide stabilizer, wherein the activation part and the peroxide part are each flowable compositions.

11 Claims, 4 Drawing Sheets

TWO-PART TOOTH WHITENING COMPOSITION AND SYSTEM, AND METHODS OF USING THE SAME

CROSS-REFERENCE TO RELATED APPLICATION

The benefit under 35 U.S.C. §119(e) of U.S. Provisional Patent Application No. 61/613,955, filed Mar. 21, 2012, is hereby claimed, and the disclosure is incorporated herein by reference in its entirety.

BACKGROUND

1. Field of the Disclosure

The disclosure relates generally to a tooth whitening composition and methods of using the same to whiten one or more teeth, and more particularly, to a tooth whitening composition provided as a two part composition and method of using the same.

2. Brief Description of Related Technology

In recent years, tooth whitening has become popular with many consumers, as many desire to have a white and bright smile. Tooth whitening procedures are non-surgical and non-invasive. Clinical studies have shown the tooth whitening can be a safe and easy cosmetic procedure to provide a consumer with a bright confident smile. Consumers' selection of a whitening method is often affected by several factors, including, for example, whitening efficiency, safety, side effects, ease of use, cost, and type of tooth discoloration to be treated.

A major ingredient in most tooth whitening products is peroxide. The peroxide must be provided in a sufficient amount and in an active state in order to effect whitening of the teeth and achieve the desired whitening effect. However, inclusion of the peroxide component at high levels can also result in adverse side-effects, such as tooth sensitivity. Additionally, the peroxide must be contained in the composition during storage in an inactive state so that the whitening composition remains stable and has a suitable shelf life. It has been a challenge in the art to balance these considerations and provide a composition that is stable enough to be stored for a sufficient amount of time and has the appropriate and desired activity of the peroxide at the moment of use.

Conventional tooth whitening compositions attempt to solve the stability and shelf life problems associated with use of peroxide by providing peroxide stabilizers that keep the peroxide inactive during storage. Such stabilizers include, for example, stannate, 8-hydroxyquinonline pyrophosphate, and ethylenediamine tetra-acetate. For example, U.S. Pat. No. 6,514,543 discloses a multi-component peroxide-based whitening formulation, with the peroxide portion including a hydrogen peroxide precursor, an anhydrous carrier, a thickener, and a peroxide stabilizer. While these stabilizers are effective in maintaining the stability of the peroxide during storage, they adversely affect the performance of the whitening composition by reducing the efficiency of the peroxide in being able to break down stains. Furthermore, use of the stabilizers adversely delays the time in which the peroxide becomes activated once applied to a tooth.

In order to prevent adverse side effects, such as sensitivity, tooth whitening compositions generally remain on a tooth for a short time frame of about five minutes to about 30 minutes. The delay in peroxide activation caused by the use of peroxide stabilizers adversely limits the whitening affect that can be achieved by conventional compositions containing peroxide stabilizers in this short application time frame. Thus, there is a need in the art to provide a stable peroxide-based tooth whitening composition that is able to activate substantially immediate once applied to a tooth so that the whitening efficiency of the composition is maximized during the application time.

U.S. Pat. No. 6,746,664 is another example of a conventional whitening system that includes a bleaching agent component and a separate neutralizing agent and thickener that is water free. Such water free systems are gel-based formulations. Gel-based whitening formulations disadvantageously have reduced whitening efficiency as compared to flowable compositions because of the slower rate at which gel-based formulation can diffuse into the tooth enamel.

U.S. Pat. No. 7,802,988 illustrates another conventional whitening system in which a whitening formulation is activated by an external laser light. The system described in U.S. Pat. No. 7,802,988 is not designed for consumer use. It requires that gums of the patient and other soft tissue be protected from exposure to the laser light. Furthermore, such compositions can be more difficult and expensive to formulate as they require the addition of photo-absorbing agents for activation.

These and other disadvantages of conventional whitening formulations are overcome by the disclosed whitening composition.

SUMMARY

In accordance with an embodiment of the disclosure, a tooth whitening composition includes an activation part comprising a peroxide activating component, and a peroxide part comprising a peroxide component. The peroxide part does not contain (i.e., is free of) a peroxide stabilizer. The peroxide part and the activation part can be combined by mixing just prior to application to at least one tooth to form the tooth whitening composition.

In accordance an embodiment of the disclosure, a tooth whitening system includes an activation part comprising a peroxide activating component provided in a first container, and a peroxide part comprising a peroxide component provided in a second container. The peroxide part does not contain a peroxide stabilizer.

In accordance with an embodiment of the disclosure, method of whitening at least one tooth includes combining an activation part containing a peroxide activating component with a peroxide part containing a peroxide component to form a tooth whitening composition just prior to application, and applying the tooth whitening composition to at least one tooth. The peroxide part does not contain a peroxide stabilizer.

DETAILED DESCRIPTION

Figure 1:
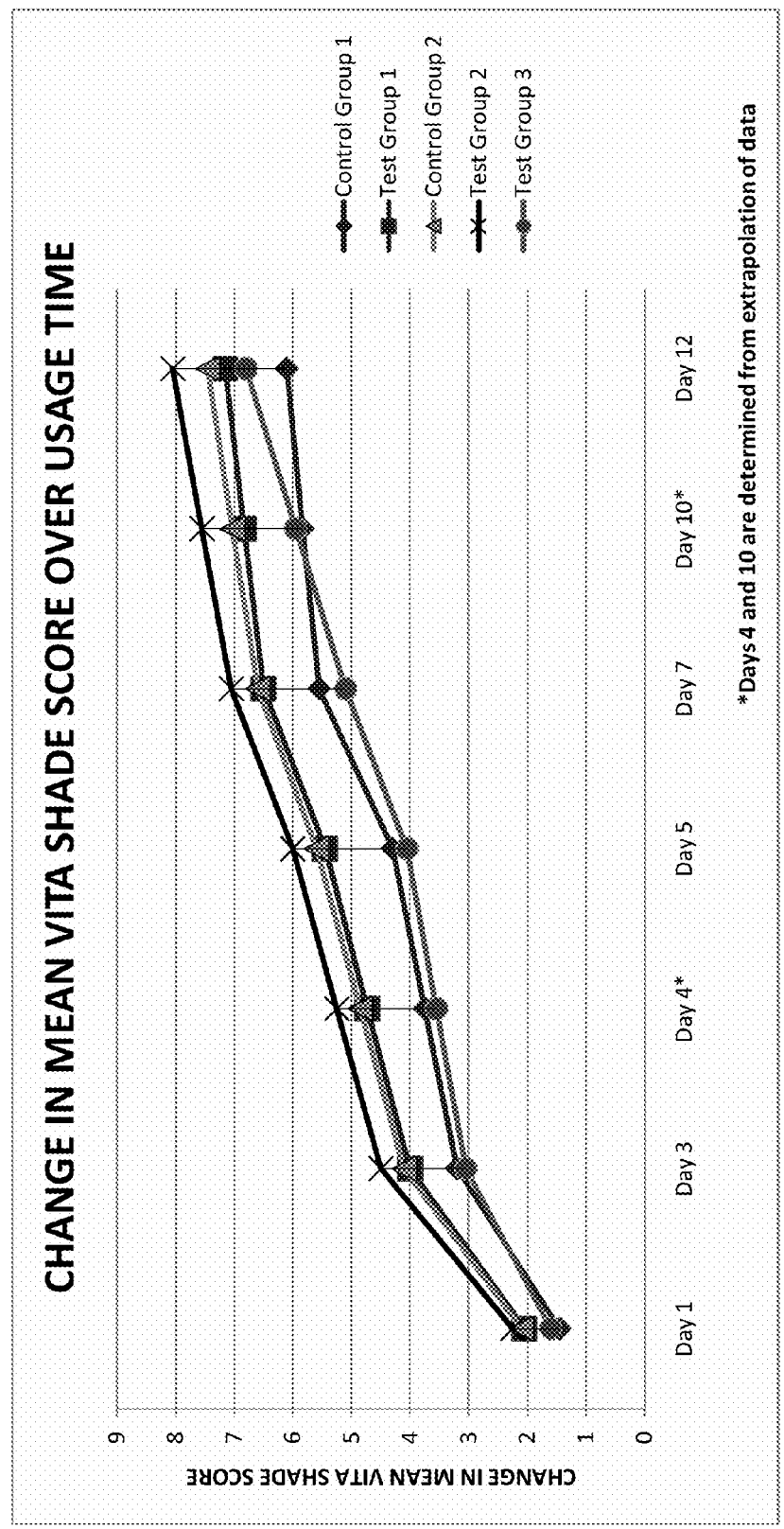
FIG. 1 is a graph showing the change in the mean Vita shade score for subjects using a conventional composition (control composition) and subjects using a composition in accordance with an embodiment of the disclosure (test composition)

Unless otherwise specified, weight percentages are expressed herein as the percentage of the component based on the total weight of the activation part or the total weight of the peroxide part, depending upon the part in which the component is provided.

In accordance with an embodiment of the disclosure, a tooth whitening composition is provided as a two-part composition, with each part being separated during storage. The first part is an activation part and can include a peroxide activating component. The second part is a peroxide part and can include a peroxide component, without the need to include a peroxide stabilizer. In some embodiments, the peroxide part is free of a peroxide stabilizer.

The whitening compositions of the disclosure advantageously provide a stable peroxide-based composition that can be stored for extended periods of time without the need for inclusion of peroxide stabilizers that adversely affect the whitening efficiency of the peroxide component. As a result of the exclusion of peroxide stabilizers, the peroxide component of the whitening compositions of the disclosure are active immediately upon application of the whitening composition to a tooth. Furthermore, the whitening compositions of the disclosure advantageously allow for whitening products to be provided with various peroxide contents without the need for complete reformulation of the entire whitening composition. For example, consumers may desire different level of whitening or have a need, for example, for reduced levels of the peroxide component due to various sensitivities to peroxide. Different whitening products, having different levels of whitening, can simply be provided using the compositions of the disclosure by adjusting the concentration of the peroxide component in the peroxide part, and without the need to reformulate the activation part. Thus, the compositions of the disclosure also provide an economical means for providing a whitening product line having a variety of whitening levels.

The whitening compositions in accordance with embodiments of the disclosure can be a flowable composition. As used herein, "flowable composition" refers to a composition that generally has a viscosity in a range of about 1 cps to about 2000 cps and is not a gel. It has advantageously been recognized that such flowable compositions are able to diffuse into tooth enamel more quickly than gels, thereby improving the whitening efficiency of the whitening composition.

In various embodiments of the disclosure, the activate part and the peroxide part can both include water.

A whitening composition in accordance with an embodiment of the disclosure was found to whiten teeth, on average, about seven shades whiter, based on the Vita shade score, with use of the composition twice daily for twelve days. Results as high as an eleven shade improvement were achieved with compositions in accordance with the disclosure. There was little to no gum irritation or tooth sensitivity reported with use of the composition. The composition is also safe for use with crowns, veneers, fillings, and other dental material. In one study, a composition in accordance with an embodiment of the disclosure was found to improve the whiteness of a subject's teeth having both surface and deep stains an average of three shades in about three days of use.

The whitening compositions of the disclosure also have a pH that is beneficial for protecting tooth enamel. Many conventional tooth whitening compositions having stabilizers for the peroxide component are provided at an acidic pH, such as a pH of 4 or 5. Such pH levels are needed in these compositions in order to maintain stability. Such acidic compositions have the potential to damage tooth enamel during the whitening process. In contrast, once the activation part and the peroxide part are mixed, the tooth whitening composition has a neutral or slightly basic pH that is not harmful to tooth enamel. For example, the tooth whitening composition can have a pH of about 7 to about 9. Other suitable pHs include, for example, pH 7, pH 8, and pH 9. A whitening composition having such a pH can also beneficially result in reduced sensitivity during the whitening process.

The activation part can include any suitable peroxide activating components. For example, suitable peroxide activating agents can include pH adjusting agents (for making the combined composition alkaline pH of 7 to 10) and catalysts, such as enzymes. Suitable peroxide activating agents can include, for example, sodium tripolyphosphate, tripotassium phosphate, KOH, NaOH, $NaHCO_3$, organic amines, such as triethylamine, salts of boric acid, catalase, vegetative enzyme extract, peroxidase, dopamine β-hydroxylase, peptide glycine α-hydroxylase, and combinations thereof. In some embodiments, the peroxide activating component can include multiple peroxide activating materials. For example, sodium tripolyphosphate and tripotassium phosphate can each be included in the activation part. For example, sodium tripolyphosphate and/or tripotassium phosphate can be included in combination with a pH adjusting agent. The peroxide activating component can be included in the activation part, for example, in an amount in a range of about 1 weight percent (wt %) to about 20 wt %, about 1 wt % to about 10 wt %, about 2 wt. % to about 18 wt. %, about 4 wt. % to about 16 wt. %, about 6 wt. % to about 14 wt. %, about 8 wt. % to about 12 wt. %, about 10 wt. % to about 20 wt. %, about 12 wt. % to about 18 wt. %, about 14 wt. % to about 20 wt. %, or about 16 wt. % to about 18 wt. %. Other suitable peroxide activating component amounts include, for example, about 1, 2, 3, 4, 5, 6, 7, 8, 9, 10, 11, 12, 13, 14, 15, 16, 17, 18, 19, or 20 wt. %.

The activation part also includes a solvent. The solvent can be included in the activation part in an amount, for example, in a range of about 1 wt. % to about 90 wt. %, about 5 wt. % to about 80 wt. %, about 10 wt. % to about 70 wt. %, about 20 wt. % to about 60 wt. %, or about 30 wt. % to about 50 wt. %. Other suitable amounts of the solvent include, for example, about 1, 2, 3, 4, 5, 6, 7, 8, 9, 10, 15, 20, 25, 30, 35, 40, 45, 50, 55, 60, 65, 70, 75, 80, 85, or 90 wt. %. The solvent can be, for example, water. Advantageously, the activation part is aqueous. The activation part can further include, additional solvents such as, but are not limited to, acetone, ethanol, isopropyl alcohol, methanol, butyl alcohol, hexane, and combinations thereof.

The activation part can also include a carrier or rheology modifying agent. The carrier or rheology modifying agent can be included in the activation part, for example, in an amount in a range of about 1 wt % to about 80 wt %, about 10 wt % to about 70 wt %, about 15 wt % to about 60 wt %, about 20 wt % to about 50 wt %, about 30 wt % to about 40 wt %, about 50 wt % to about 80 wt %, about 45 wt % to about 75 wt %, about 1 wt % to about 20 wt %, about 1 wt % to about 10 wt %, about 2 wt. % to about 18 wt. %, about 4 wt. % to about 16 wt %, about 6 wt. % to about 14 wt. %, about 8 wt. % to about 12 wt. %, about 10 wt. % to about 20 wt. %, about 12 wt. % to about 18 wt. %, about 14 wt. % to about 20 wt. %, or about 16 wt. % to about 18 wt. %. Other suitable carrier or rheology modifying agent amounts include, for example, about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, and 80 wt. %.

For example, the carrier or rheology modifying agent can include a polyol. For example, the polyol carrier can be triethylene glycol, propylene glycol, glycerin, polyvinyl alcohols, polyethylene glycol, polyvinyl alcohol copolymer, erythritol, arabitol, xylitol, ribitol, mannitol, sorbitol, dulcitol, iditol, isomalt, malitol, lacitol, polyglycitol, and combinations thereof.

Advantageously, by separating the peroxide component into a separate part of the tooth whitening composition until just prior to application, the whitening composition can further include other optional ingredients to expand the performance of the tooth whitening composition beyond whitening of a tooth, without adversely affecting the stability of the peroxide component. For example, the activation part can optionally include one or more agents that promote general oral health, such as, for example, a cavity prevention agent, an anti-gingivitis agent, and a dental tartar reducing agent. For example, the activation part can include xylitol, which can promote cavity prevention. The activation part can also or alternatively include, for example, Gantrez® S97, available from Ashland (Wayne, N.J.), which is known to provide anti-gingivitis activity and tartar control. Gantrez S97 is a polyvinylmethyl ester maelic acid copolymer. Other suitable dental health promoting agents can include, for example, sodium tripolyphosphate, which can act as an agent to reduce tartar formation. These and any other oral health promoting agents can be provided in any suitable amounts. For example, in one embodiment, the activation part comprises xylitol in an amount of about 10 wt % to about 16 wt % and/or Gantrez S97 in an amount of about 3 wt % to about 8 wt %.

The activation part can also include a tooth desensitizing agent, for example. The tooth desensitizing agent can aid in lessening or preventing tooth sensitivity resulting from the whitening formulation. The tooth desensitizing agent can be included in the activation part, for example, in an amount in a range of about 1 wt. % to about 10 wt. %, about 2 wt. % to about 8 wt. %, about 3 wt. % to about 6 wt. %, about 1 wt. % to about 7 wt. %, or about 2 wt. % to about 7 wt. %. Other suitable amounts of desensitizing agent include, for example, about 1, 2, 3, 4, 5, 6, 7, 8, 9, or wt. %. The desensitizing agent can be for example, potassium nitrate, strontium chloride, sodium fluoride, ferric oxalate, and combinations thereof.

The peroxide part of the composition includes a peroxide component and a solvent for the peroxide component. The peroxide part does not include any peroxide stabilizers. Advantageously, the two-part composition of the disclosure allows for inclusion of a stable peroxide component without the need for peroxide stabilizers. In one embodiment, the peroxide part consists essentially of a peroxide component. For example, in one embodiment, the peroxide part includes only the peroxide component and a solvent, for example, water.

The peroxide component can be, for example, hydrogen peroxide, urea peroxide, PVP-hydrogen peroxide complex, and combinations thereof. The peroxide component can be provided in the peroxide part in an amount, for example, in a range of about 10 wt % to about 80 wt %, about 15 wt % to about 70 wt %, about 20 wt % to about 60 wt %, about 50 wt % to about 80 wt %, about 40 wt % to about 80 wt %, or about 50 wt % to about 70 wt %. Other suitable amounts of the peroxide component include, for example, about 10, 15, 20, 25, 30, 35, 40, 45, 50, 55, 60, 65, 70, 75, and 80 wt %. For example, in one embodiment, the peroxide part includes about 24 wt % of the peroxide component.

The peroxide part can further include a solvent that is compatible with the peroxide component. For example, the solvent can be water. The solvent can be provided in the peroxide part, for example, in an amount in a range of about 20 wt % to about 90 wt %, about 30 wt % to about 80 wt %, about 40 wt % to about 70 wt %, about 50 wt % to about 60 wt %, or about 50 wt % to about 70 wt %. For example, in one embodiment, the solvent is water and the peroxide part includes about 32 wt % water.

The activation part and the peroxide part can each have a viscosity in a range of about 1 cps to about 2000 cps, measured at room temperature (about 20° C. to about 25° C.). Other suitable ranges include, for example, about 5 cps to about 1500 cps, about 10 cps to about 1000 cps, about 40 cps to about 800 cps, about 50 cps to about 700 cps, about 60 cps to about 500 cps, about 100 cps to about 400 cps, about 200 cps to about 300 cps, about 1 cps to about 10 cps, about 1 cps to about 100 cps, about 10 cps to about 80 cps, about 20 cps to about 50 cps, about 200 cps to about 2000 cps, about 400 cps to about 1000 cps, about 600 cps to about 900 cps, about 800 cps to about 2000 cps, about 1000 cps to about 2000 cps, about 700 cps to about 1500 cps, about 600 cps to about 2000 cps, about 300 cps to about 1800 cps, about 100 cps to about 1000 cps, about 300 cps to about 900 cps, and about 500 cps to about 700 cps, as measured at 20° C. (room temperature). For example, the viscosity can be about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900 950, 1000, 1100, 1200, 1300, 1400, 1500, 1600, 1700, 1800, 1900, or 2000 cps, measured at 20° C. (room temperature). The viscosity can be adjusted to allow for a variety of application methods, including, for example, application by a brush, pad, ampoule, capsule, syringe, swab, sponge, pen, or other applicator. In one embodiment the activation part and the peroxide part are provided as flowable liquids, which can beneficially allow for the parts to be uniformly mixed, for example, when provided in an ampoule type applicator.

In accordance with embodiments of the disclosure, the activation part and the peroxide part can be provided in separate containers and then combined by mixing just prior to use in order to active the peroxide component and form the tooth whitening composition. Once the parts are mixed, the tooth whitening composition can be applied to at least one tooth using any known application method and/or applicator. The tooth whitening composition can be allowed to remain on the tooth in a range of about 1 minute to about 30 minutes, about 2 minutes to about 25 minutes, about 4 minutes to about 20 minutes, about 6 minutes to about 15 minutes, about 8 minutes to about 10 minutes, or about 10 minutes to about 20 minutes. Other suitable times include, for example, about 1, 2, 3, 4, 5, 6, 7, 8, 9, 10, 11, 12, 13, 14, 15, 16, 17, 18, 19, or 20 minutes.

Additional whitening enhancers can be used along with the tooth whitening composition, such as, for example, pre-whitening gels and whitening lights. For example, Pre-Whitening Amplifier Gel (GOSMILE Inc, CA) can be used as a whitening enhancer. For example, in one embodiment a pre-whitening gel can be applied to at least one tooth prior to applying the tooth whitening composition. A whitening light, such as an LED light, can also be used in combination with the tooth whitening composition. For example, the tooth whitening composition can be applied to at least one tooth and then the coated tooth can be exposed to a whitening light. U.S. patent application Ser. No. 13/165,408, the disclosure of which is in corporate herein it its entirety, discloses an example of a suitable whitening light.

The activation part and the peroxide part are separated during storage. The activation and peroxide parts can be mixed in any suitable fashion to form the tooth whitening composition just prior to use.

The activation part can be about 20 wt % to about 80 wt %, about 30 wt % to about 70 wt %, about 40 wt % to about 60 wt %, about 25 wt % to about 75 wt %, about 20 wt % to about 50 wt %, about 20 wt % to about 35 wt %, and about 40 wt % to about 80 wt % based on the total weight of the composition (the combination of the activation and the whitening parts). Other suitable amounts include, for example, about 20, 25, 30, 35, 40, 45, 50, 55, 60, 65, 70, 75, and 80 wt % based on the total weight of the composition.

The peroxide part can be about 20 wt % to about 80 wt %, about 30 wt % to about 70 wt %, about 40 wt % to about 60 wt %, about 25 wt % to about 75 wt %, about 20 wt % to about 50 wt %, about 20 wt % to about 35 wt %, and about 40 wt % to about 80 wt % based on the total weight of the composition. Other suitable amounts include, for example, about 20, 25, 30, 35, 40, 45, 50, 55, 60, 65, 70, 75, and 80 wt % based on the total weight of the composition.

In an embodiment, the activation part and the peroxide part are provided in separate containers, for example, with each container containing a single dose of the activation part and a single dose of the peroxide part. For example, a tooth whitening kit can include the activation part and the peroxide part provided in separate containers. For example, a single dose of the activation part can be provided in a first container and a single dose of the peroxide part can be provided in a second container. The first and second containers each be contained in third container, such that upon application of pressure on the external surface of the third container, the first and second containers rupture and release the activation and peroxide parts, thereby allowing them to mix in the third container.

In another embodiment, the activation part and the peroxide part can be provided in a single container separated by a removable or rupturable separator. Just prior to use the separator can be removed or ruptured to allow for mixing of the activation part and the peroxide part to form the tooth whitening composition.

In one embodiment, the composition is provided in a single-dose ampoule-type device. The single-dose ampoule device can have two ampoules within a plastic cylinder. One ampoule of the device contains the activation part, while the other ampoule contains the peroxide part. Each ampoule contains a single dose of the respective part. The composition can formed by breaking the ampoules to release the activation and peroxide parts of the composition contained therein and mix the activation and peroxide parts to form the whitening composition. The whitening composition can then be applied to at least one tooth, for example, via a brush provided at an end of the plastic cylinder. U.S. Pat. No. 7,201,577, the disclosure of which is incorporated herein by reference in its entirety, describes a single ampoule applicator, which can be suitably modified to include a second ampoule to allow for storage and application of the composition.

Additional aspects and details of the invention will be apparent from the following examples, which are intended to be illustrative rather than limiting.

EXAMPLES

Example 1

A tooth whitening composition was prepared by separately forming an activation part and a peroxide part. The activation part was formed by mixing the various components in the weight percents listed in Table 1 below.

The activation part was made by dissolving potassium nitrate in deionized water in a clean and dry mixing vessel. Tripotassium phosphate and xylitol were then added to the dissolved potassium nitrate and mixed for 45 minutes until dissolved. Gantrez S97 and propylene glycol were then added and mixing was continued for about 60 minutes at 30 rpm to form a homogenous solution.

The activation part had a viscosity of about 4 cps to about 20 cps, as measured with a UL Enhanced Adapter at 60 nm on a Brookfield DV-E Viscometer and a pH of about 9-10.

The peroxide part was formed by mixing hydrogen peroxide with water. The hydrogen peroxide was 24 wt % of the peroxide part, based on the total weight of the peroxide part, and the water was 76 wt %. The peroxide part had a viscosity of about 1 cps to about 5 cps, as measured with a UL Enhanced Adapter at 60 nm on a Brookfield DV-E Viscometer, and a pH of about 2 to 4

TABLE 1

Two-Part Whitening Composition

| | INGREDIENT | FUNCTION | AMOUNT (% BY WEIGHT OF THE TOTAL OF THE RELEVANT PART) |
|---|---|---|---|
| Activation Part | Propylene Glycol | Carrier | 11.08 |
| | Deionized Water | Solvent | 60.55 |
| | Gantrez ® S97 | Anti-gingivitis and tartar prevention agent | 4.13 |
| | Xylitol | Anti-cavity agent | 14.74 |
| | Sodium tripoly-phosphate | Peroxide activating component | 2.50 |
| | Tripotassium phosphate | Peroxide activating component | 2.00 |
| | Potassium nitrate | Desensitizing agent | 5.00 |
| | Total | | 100 wt. % |
| Peroxide Part | Hydrogen Peroxide (35% solution) | Peroxide component | 68.6 |
| | Deionized water | Solvent | 31.4 |
| | Total | | 100 wt % |

The two parts were combined to form a tooth whitening composition in accordance with an embodiment of the disclosure. The combined composition had a viscosity of about 2 cps to about 10 cps, as measured with a UL Enhanced Adapter at 60 nm on a Brookfield DV-E Viscometer, and a pH of about 7 to 9.

Example 2

The whitening effect of the compositions in accordance with the disclosure ("the test composition") were tested by comparison to a control whitening composition, the GOS-MILE Smile Whitening System, a commercially available single-part whitening system ("the control composition"). The control composition is an alcohol-based single part peroxide-based whitening composition. The composition in accordance with the disclosure used as the test composition is described in Example 1. The test and control compositions were also tested with and without the supplemental use of an LED light. The compositions were each used for a total of twelve days. The subjects were measured, according to the Vita shade score scale, at day 0, before and after the first application of the test or control composition, and at days 3, 5, 7, and 12. The study testing groups are described in Table 2 below:

TABLE 2

Study Groups

| Group | Whitening System | Usage |
|---|---|---|
| Control Group 1 | GOSMILE Smile Whitening System (a single part composition) | 2x daily for 12 days |
| Test Group 1 | Composition of Example 1 | 2x daily for 12 days |
| Control Group 2 | GOSMILE Smile Whitening System (a single part composition) + LED Light | 3x daily with 3 ten minute cycles with the LED light after application of the composition for 12 days |
| Test Group 2 | Composition of Example 1 + LED Light | 3x daily with 3 ten minute cycles with the LED light after application of the composition for 12 days |
| Test Group 3 | Composition of Example 1 + LED Light + Pre-whitening gel swabs | 3x daily application of the swabs and then the composition, with 3 ten minute cycles with the LED light after application of the composition for 12 days |

The study was conducted using a double-blind research protocol that complied with industry and ADA standards. The subjects were selected from a pool of subjects in south Florida and randomly assigned to one of the control or the test groups. Twenty subjects were enrolled in each of the groups (100 total subjects in the study). All subjects were residents of south Florida and all major races were represented in the study group. All subjects were healthy and had healthy, natural maxillary teeth that were judged to have a Vita shade of A3 or darker. Each group also included ten subjects that had at least one crown, veneer, or e aesthetic tooth colored dental restorations. Each group was balanced for mean age and gender, except Test Group 3 had significantly older subjects. The older subjects in Test Group 3 allowed for testing of the test composition in an older population with teeth that contained deep set stains. The demographics of the study groups is provided in Table 3 below. There was no statistical difference in age, race, or gender between the groups, except with Test Group 3, the age was statistically higher.

TABLE 3

Demographics of the Subjects in the Study Groups

| Group | Mean Age | Race | Male:Female Ratio |
|---|---|---|---|
| Control Group 1 | 38.0 ± 14.7 | 12 White; 3 Black 2 Hispanic; 3 Asian | 10:10 |
| Test Group 1 | 37.6 ± 14.4 | 11 White; 2 Black 2 Hispanic; 5 Asian | 10:10 |
| Control Group 2 | 37.8 ± 16.2 | 11 White; 3 Black 4 Hispanic; 2 Asian | 10:10 |
| Test Group 2 | 38.3 ± 16.1 | 12 White; 2 Black 3 Hispanic; 3 Asian | 10:10 |
| Test Group 3 | 59.5 ± 6.6 | 11 White; 4 Black 2 Hispanic; 3 Asian | 10:10 |

Note:
there was no statistical difference between Control Groups 1 and 2 and Test Groups and 2. Test Group 3 is significantly older in order to determine deep stain removability.

The assigned composition was delivered to the subjects in plain white paper bags, with instructions for use.

The following measurements of safety and efficacy were collected on examinations on day 0 (before and after use), day 3, day 5, day 7, and day 12:
- Oral hard and soft tissue evaluation
- Assessment for adverse reactions
- Löe and Silness Gingival Index Score
- Visual Analog (V.A.S.) dental hypersensitivity score
- Vita shade score (human clinical assessment of efficacy of teeth whitening)
- Spectrophotometer assessment of tooth lightness.

The use of twenty subjects in each group allowed for sufficient data to detect statistical differences in mean tooth shades of ±0.05 with a high degree of confidence of the data being accurate. The data was collected at each examination interval and compared between groups using a two-group Students t-Test for independent samples. When three or more groups were compared simultaneously, ANOVA was used. All statistical analyses were conducted using standard statistical software using a level of significance of $p<0.05$.

The whitening efficacy was judged using the Vita shade score scale, with confirmation of the results with a Minolta CR-321 spectrophotometer according to ADA guidelines and industry standards. The mean Vita shade scores as measured on the measurement days are provided in Table 4 below, and extrapolated (non-measured) scores for days 4 and 10 are also provided. There was no statistical difference in the baseline scores between the control and test groups, except that Test Group 3 was purposely populated with older people with teeth that had deep set stains and thus started with statistically darker teeth at baseline.

TABLE 4

Mean Vita Shade Scores at Each Examination Interval

| Group | Baseline | Day 1 | Day 3 | Day 4* extrapolated value | Day 5 | Day 7 | Day 10* extrapolated value | Day 12 |
|---|---|---|---|---|---|---|---|---|
| Control Group 1 | 9.85 | 8.40 | 6.65 | 6.10 | 5.55 | 4.30 | 4.03 | 3.75 |
| Test Group 1 | 9.85 | 7.80 | 5.85 | 5.13 | 4.40 | 3.35 | 3.03 | 2.70 |
| Control Group 2 | 9.85 | 7.75 | 5.75 | 5.00 | 4.25 | 3.25 | 2.83 | 2.40 |
| Test Group 2 | 9.85 | 7.6 | 5.35 | 4.60 | 3.85 | 2.80 | 2.30 | 1.80 |
| Test Group 3 | 10.85 | 9.25 | 7.80 | 7.30 | 6.80 | 5.75 | 4.90 | 4.05 |

Figure 2:
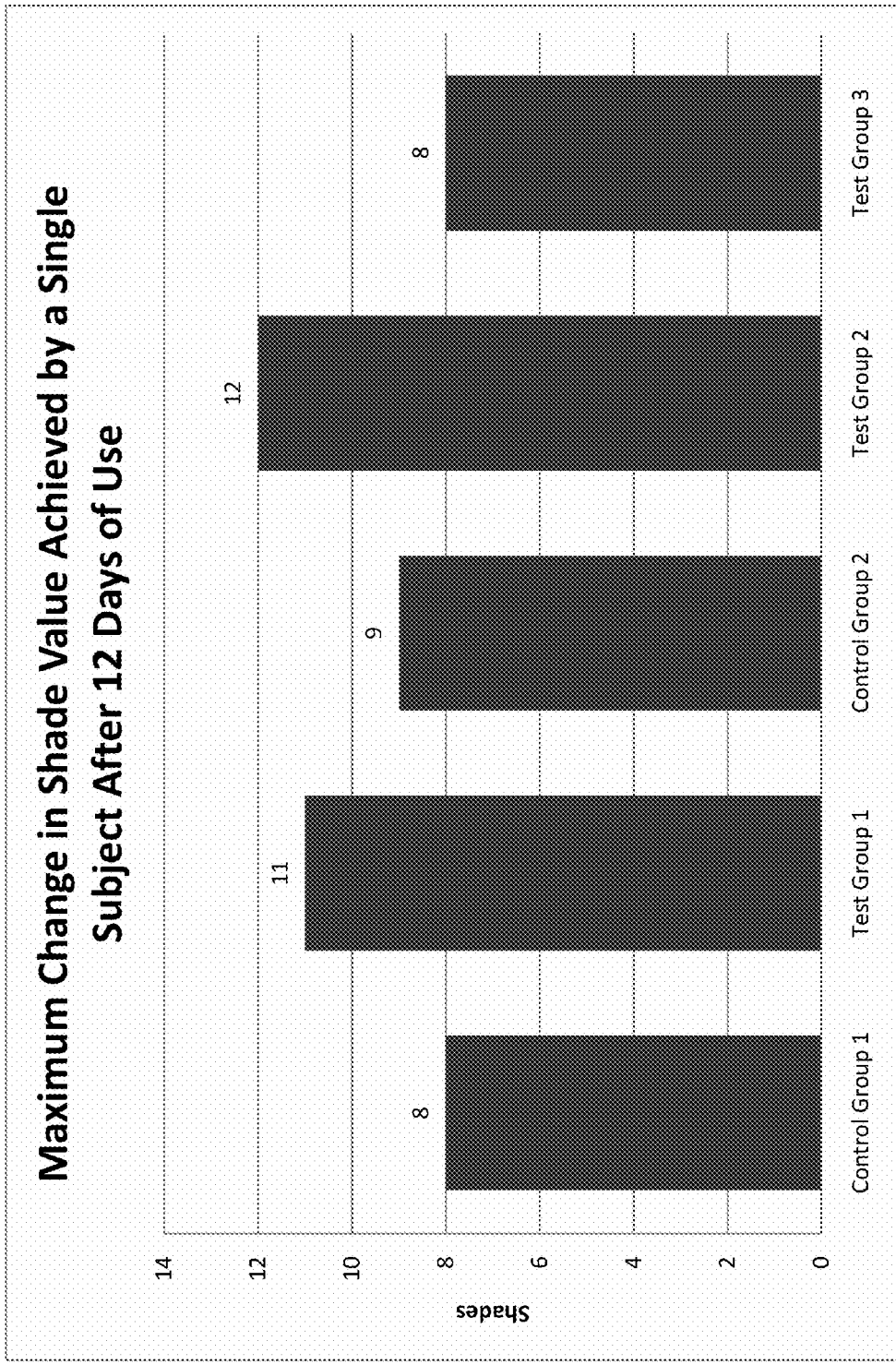
FIG. 2 is a graph showing the maximum shade difference, as measured by the Vita shade score, observed for subjects using a conventional composition (control composition) and subjects using a composition in accordance with an embodiment of the disclosure (test composition.

The table below shows the mean improvement in shades for each of the measured days and extrapolated values for days 4 and 10. After three days of use, all groups had mean vita shade scores that were statistically less than the starting shade. Test Group 1 demonstrated a significant improvement in whiteness after three days as compared to control group 1. Control Group 1 demonstrated an improvement of about 3 shades after 3 days, and Test Group 1 demonstrated an improvement of about 4 shades after 3 days. Similarly, Test Group 2 demonstrated a significant improvement in whiteness after 3 days as compared to Control Group 2. Control Group 2 demonstrated an improvement of about 4 shades and Test Group 2 demonstrated an improvement of about 4.5 shades. The improvement in whiteness demonstrated by Test Group 3 evidences that the composition in accordance with the disclosure is suitable and effective for use to remove deep set stains. The significantly improved whitening performance of the test composition was even more pronounced after 12 days of use as shown in Table 5 below. FIG. 1 graphically illustrates the mean change in Vita shade score and FIG. 2 illustrates the maximum results achieved for each group.

TABLE 5

Change in Mean Vita Shade Score At Each Examination Interval

| Group | Day 1 | Day 3 | Day 4* extrapolated value | Day 5 | Day 7 | Day 10* extrapolated value | Day 12 |
|---|---|---|---|---|---|---|---|
| Control Group 1 | 1.45 | 3.20 | 3.75 | 4.30 | 5.55 | 5.83 | 6.10 |
| Test Group 1 | 2.05 | 4.00 | 4.73 | 5.45 | 6.50 | 6.83 | 7.15 |
| Control Group 2 | 2.10 | 4.10 | 4.85 | 5.60 | 6.60 | 7.03 | 7.45 |
| Test Group 2 | 2.25 | 4.5 | 5.25 | 6.00 | 7.05 | 7.55 | 8.05 |
| Test Group 3 | 1.60 | 3.05 | 3.55 | 4.05 | 5.10 | 5.95 | 6.80 |

Figure 3:
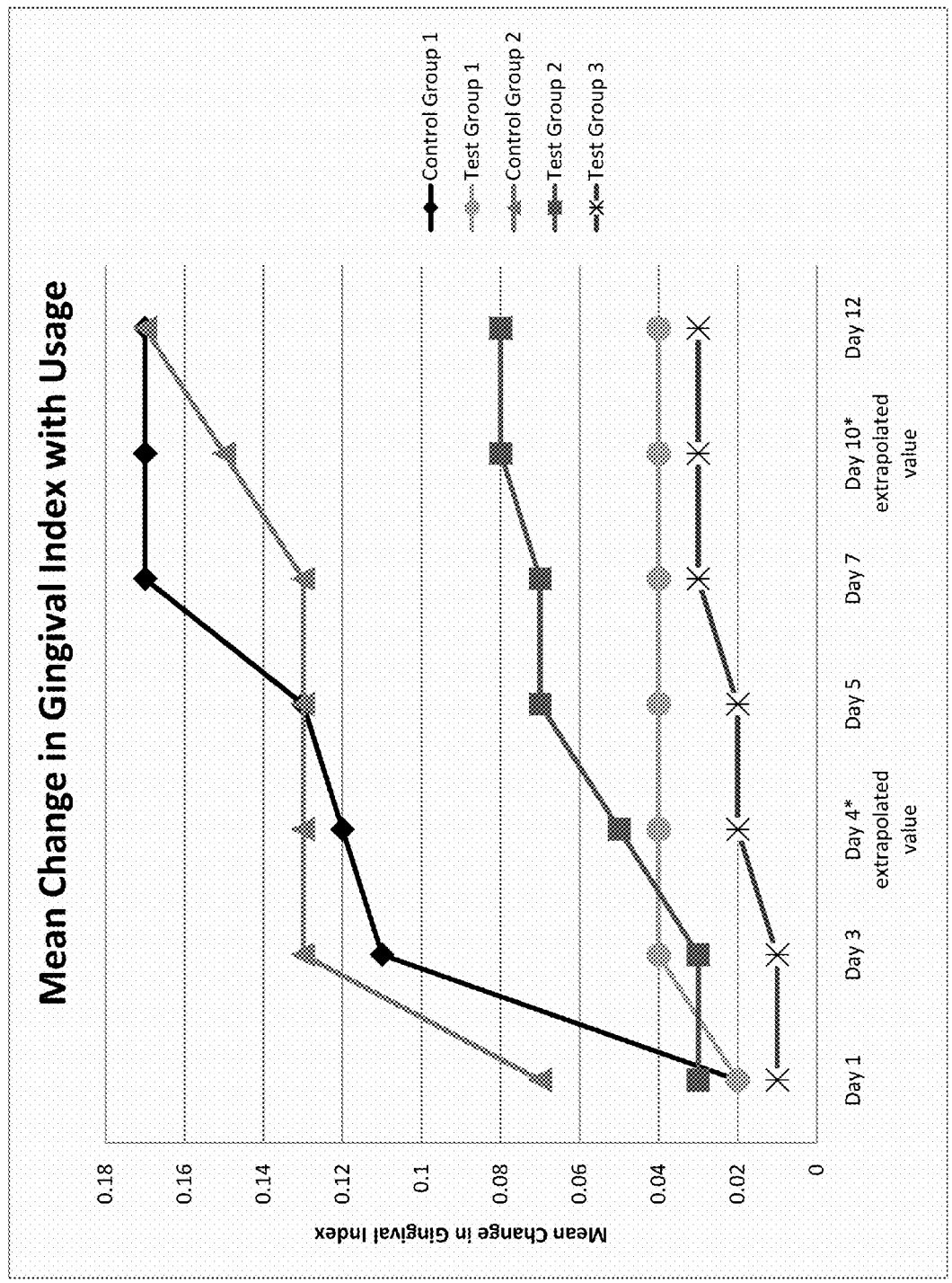
FIG. 3 is a graph showing the mean change in gingival index with usage for subjects using a conventional composition (control composition) and subjects using a composition in accordance with an embodiment of the disclosure (test composition.

Safety of the test composition evaluated using the Loe and Silness Gingival Index scoring, VAS Sensitivity Index scoring, and through thorough monitoring of the hard and soft tissue oral health of the subjects. All tested compositions (control and test compositions) were judged to be safe, with no adverse reactions or serious side effects resulting in any of the subjects tested. In general, there was no tissue changes found in any of the study groups except for very mild, reversible blanching/bleaching of the marginal gingival in about 5% of subjects studied. The compositions in accordance with the disclosure were observed to cause less tissue change as compared to the control composition. None of the subjects experienced any statistically significant amount of gum irritation. However, the test composition had statistically significant ($p<0.0001$) less gum irritation as compared to the control composition over the twelve day use period. The mean change in the gingival index score as compared to the baseline taken at day 0 is shown in Table 6, below. FIG. 3 graphically illustrates these results.

TABLE 6

Mean Change in Gingival Index Score as Compared to Baseline

| Group | Day 1 | Day 3 | Day 4* extrapolated value | Day 5 | Day 7 | Day 10* extrapolated value | Day 12 |
|---|---|---|---|---|---|---|---|
| Control Group 1 | 0.02 | 0.11 | 0.12 | 0.13 | 0.17 | 0.17 | 0.17 |
| Test Group 1 | 0.02 | 0.04 | 0.04 | 0.04 | 0.04 | 0.04 | 0.04 |
| Control Group 2 | 0.07 | 0.13 | 0.13 | 0.13 | 0.13 | 0.15 | 0.17 |
| Test Group 2 | 0.03 | 0.03 | 0.05 | 0.07 | 0.07 | 0.08 | 0.08 |
| Test Group 3 | 0.01 | 0.01 | 0.02 | 0.02 | 0.03 | 0.03 | 0.03 |

Figure 4:
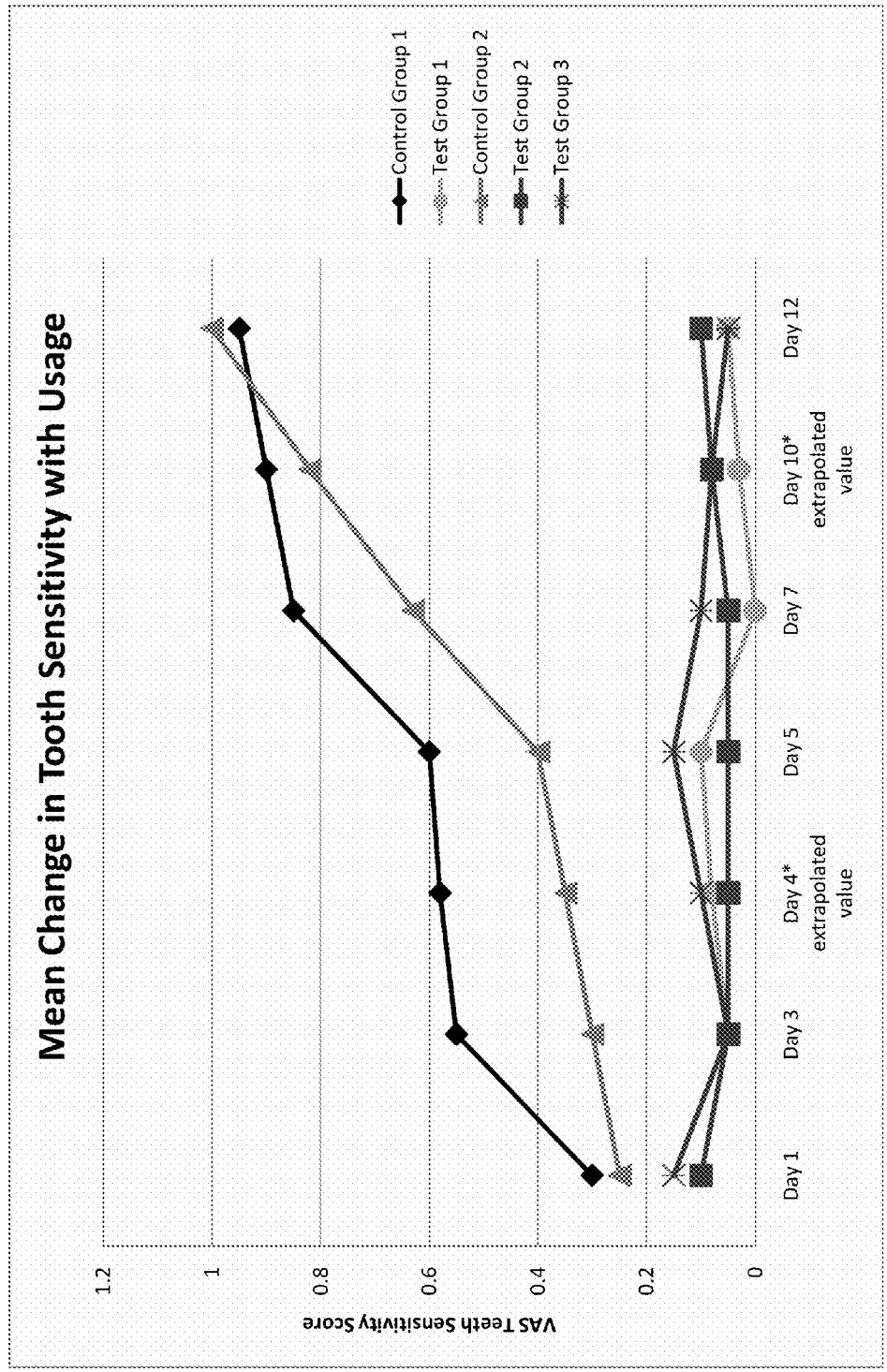
FIG. 4 is a graph showing the mean change in tooth sensitivity, as measured by the VAS teeth sensitivity score, for subjects using a conventional composition (control composition) and subjects using a composition in accordance with an embodiment of the disclosure (test composition.

It was also determined that neither the control nor the test composition resulted in a statistically significant increase in tooth sensitivity ($p>0.05$) when tested using the VAS Teeth Sensitivity scale. However, the test composition caused statistically significant ($p<0.05$) less tooth sensitivity as compared to the control composition. The mean change in VAS Teeth Sensitivity score as compared to the baseline taken at day 0 is shown in Table 7 below and graphically in FIG. 4.

TABLE 7

Mean Change in VAS Teeth Sensitivity Score as Compared to Baseline

| Group | Day 1 | Day 3 | Day 4* extrapolated value | Day 5 | Day 7 | Day 10* extrapolated value | Day 12 |
|---|---|---|---|---|---|---|---|
| Control Group 1 | 0.30 | 0.55 | 0.58 | 0.60 | 0.85 | 0.90 | 0.95 |
| Test Group 1 | 0.10 | 0.05 | 0.08 | 0.10 | 0.00 | 0.03 | 0.05 |
| Control Group 2 | 0.25 | 0.30 | 0.35 | 0.40 | 0.63 | 0.82 | 1.00 |
| Test Group 2 | 0.10 | 0.05 | 0.05 | 0.05 | 0.05 | 0.08 | 0.10 |
| Test Group 3 | 0.15 | 0.05 | 0.10 | 0.15 | 0.10 | 0.08 | 0.05 |

The safety of using the test composition with dental restorations, such as crowns, veneers, and filings, was evaluated by incorporating at least 50% subject having such dental restorations on at least one tooth. It was determined that none of these subjects experienced any damage or harm to these restorations.

As noted previously, the ability of the composition in accordance with the disclosure to lighten deep set stains was evaluated in Test Group 3. The subjects of Test Group 3 ranged from 50 to 70 years old and had darker teeth, with a baseline mean vita shade of 10.85. The combination of a pre-whitening gel, test composition, and the LED light was shown to be effective in removing deep set stains. It was also observed that the subjects of Test Group 3 experienced virtually no tooth sensitivity or gum irritation.

The invention has been described with reference to specific examples, which are intended to be illustrative only and not to be limiting of the invention. It will be apparent to those of ordinary skill in the art that changes, additions, and/or deletions may be made to the disclosed embodiments without departing from the spirit and scope of the invention.

What is claimed:
1. A tooth whitening composition consisting of:
    (a) an aqueous activation part consisting of propylene glycol, water, a polyvinylmethyl ester maelic acid copolymer, xylitol, sodium tripolyphosphate, tripotassium phosphate, and potassium nitrate, and
    (b) a peroxide part consisting of hydrogen peroxide and water.

2. The tooth whitening composition of claim 1, wherein the hydrogen peroxide is present in an amount of about 15 wt % to about 80 wt % based on the total weight of the peroxide part.

3. The tooth whitening composition of claim 1, wherein the water is present in the peroxide part in an amount of about 1 wt % to about 90 wt % based on the total weight of the peroxide part.

4. The tooth whitening composition of claim 1, wherein the pH of the composition after combination of (a) and (b) is about 7 to about 9.

5. A method of whitening at least one tooth, comprising:
   combining (a) an aqueous activation part with (b) a peroxide part to form a tooth whitening composition, wherein the aqueous activation part consists of propylene glycol, water, a polyvinylmethyl ester maelic acid copolymer, xylitol, sodium tripolyphosphate, tripotassium phosphate, and potassium nitrate, and the peroxide part consists of hydrogen peroxide and water; and
   applying the tooth whitening composition to at least one tooth.

6. The method of claim 5, further comprising allowing the tooth whitening composition to remain on the at least one tooth for about 1 minute to about 30 minutes.

7. The method of claim 5, further comprising applying a whitening light to the at least one tooth after applying the tooth whitening composition.

8. The method of claim 5, further comprising applying a pre-whitening gel prior to applying the tooth whitening composition.

9. The method of claim 5, wherein the hydrogen peroxide is present in an amount of about 15 wt % to about 80 wt % based on the total weight of the peroxide part.

10. The method of claim 5, wherein the water is present in the peroxide part in an amount of about 1 wt % to about 90 wt % based on the total weight of the peroxide part.

11. The method of claim 5, wherein the pH of the tooth whitening composition after combination of (a) and (b) is about 7 to about 9.

* * * * *